(12) United States Patent
Wenzel et al.

(10) Patent No.: US 7,848,816 B1
(45) Date of Patent: Dec. 7, 2010

(54) ACQUIRING NERVE ACTIVITY FROM CAROTID BODY AND/OR SINUS

(75) Inventors: Brian Jeffrey Wenzel, San Jose, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 280 days.

(21) Appl. No.: 11/964,865

(22) Filed: Dec. 27, 2007

(51) Int. Cl.
*A61N 1/08* (2006.01)
(52) U.S. Cl. ...................................... 607/42
(58) Field of Classification Search .............. 607/9, 607/42, 44, 45, 46
See application file for complete search history.

(56) References Cited

U.S. PATENT DOCUMENTS

| | | | |
|---|---|---|---|
| 4,201,219 A | 5/1980 | Gonzalez | |
| 5,111,815 A * | 5/1992 | Mower | 607/4 |
| 5,658,318 A | 8/1997 | Stroetmann et al. | |
| 6,073,048 A | 6/2000 | Kieval | |
| 6,850,801 B2 | 2/2005 | Kieval et al. | |
| 2005/0149128 A1 | 7/2005 | Heil | |
| 2005/0288728 A1 | 12/2005 | Libbus | |
| 2006/0089678 A1* | 4/2006 | Shalev | 607/23 |
| 2006/0095088 A1* | 5/2006 | De Ridder | 607/48 |
| 2006/0241697 A1* | 10/2006 | Libbus et al. | 607/2 |
| 2006/0259078 A1* | 11/2006 | Libbus | 607/2 |
| 2006/0282131 A1* | 12/2006 | Caparso et al. | 607/62 |
| 2007/0038262 A1 | 2/2007 | Kieval | |
| 2007/0150006 A1 | 6/2007 | Libbus et al. | |
| 2008/0015659 A1 | 1/2008 | Zhang | |
| 2008/0177365 A1 | 7/2008 | Bolea | |
| 2008/0243196 A1 | 10/2008 | Libbus | |
| 2009/0143838 A1 | 6/2009 | Libbus | |

FOREIGN PATENT DOCUMENTS

| | | |
|---|---|---|
| EP | 0481583 A2 | 4/1992 |
| EP | 0481583 A3 | 4/1992 |
| EP | 0481583 B1 | 4/1992 |

OTHER PUBLICATIONS

Non-Final Office Action mailed Sep. 3, 2009: Related U.S. Appl. No. 11/964,941.

* cited by examiner

*Primary Examiner*—Niketa I Patel
*Assistant Examiner*—Hiba El-Kaissi
(74) *Attorney, Agent, or Firm*—Theresa A. Takeuchi; Steven M. Mitchell

(57) ABSTRACT

An exemplary includes acquiring an electroneurogram of the right carotid sinus nerve or the left carotid sinus nerve, analyzing the electroneurogram for at least one of chemosensory information and barosensory information and calling for one or more therapeutic actions based at least in part on the analyzing. Therapeutic actions may aim to treat conditions such as sleep apnea, an increase in metabolic demand, hypoglycemia, hypertension, renal failure, and congestive heart failure. Other exemplary methods, devices, systems, etc., are also disclosed.

14 Claims, 11 Drawing Sheets

Chief (Glomus) Cell Unit of Carotid Body
500

ACQUIRING NERVE ACTIVITY FROM CAROTID BODY AND/OR SINUS

TECHNICAL FIELD

Subject matter presented herein generally relates to techniques to acquire nerve activity from the carotid body and/or sinus for purposes of diagnostics and/or therapy.

BACKGROUND

The ninth cranial nerve (CN IX), referred to as the glossopharyngeal nerve, includes a branch that innervates the carotid body and carotid sinus. This branch is referred to as the carotid sinus nerve (CSN), which occurs bilaterally (i.e., right CSN and left CSN). The CSN includes afferent fibers that convey information about arterial blood going to the brain. In particular, the CSN conveys chemosensory information and barosensory information. Such information can be useful alone or in conjunction with other information to treat a variety of conditions. Various techniques are described herein for acquisition, analysis and use of CSN information. Such techniques are optionally implemented in conjunction with one or more respiratory, cardiac or metabolic therapies.

SUMMARY

An exemplary includes acquiring an electroneurogram of the right carotid sinus nerve or the left carotid sinus nerve, analyzing the electroneurogram for at least one of chemosensory information and barosensory information and calling for one or more therapeutic actions based at least in part on the analysis. Therapeutic actions may aim to treat conditions such as sleep apnea, an increase in metabolic demand, hypoglycemia, hypertension, renal failure, and heart failure. Other exemplary methods, devices, systems, etc., are also disclosed.

In general, the various methods, devices, systems, etc., described herein, and equivalents thereof, are optionally suitable for use in a variety of pacing therapies, other cardiac related therapies, etc.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., described herein pertain acquiring nerve information for the right and/or left carotid sinus nerve (CSN) (also known as Hering's nerve), which is a branch of the ninth cranial nerve (CN IX), also known as the glossopharyngeal nerve (GPN). The right and left CSN include afferent fibers that convey information from a respective carotid body and carotid sinus to the brain. Information carried by the CSN includes chemical information as well as pressure information. Various exemplary technologies acquire CSN information (e.g., sensing nerve activity such as an electroneurogram, via data communication, etc.) and use the information for diagnostics and/or therapy, optionally analyzing the information prior to use.

Exemplary Stimulation Device

Figure 1:
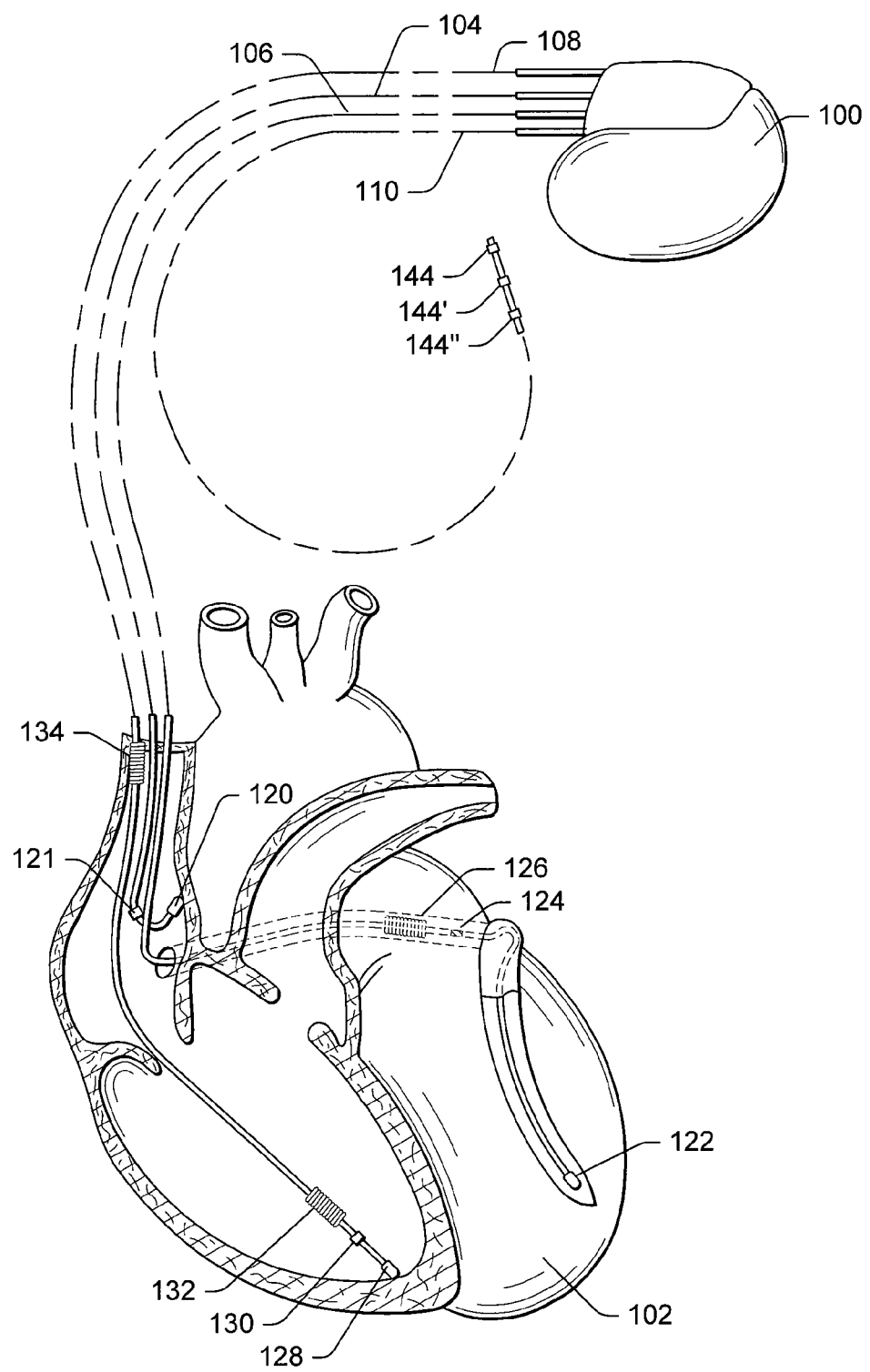
FIG. 1 is a simplified diagram illustrating an exemplary implantable stimulation device in electrical communication with three leads implanted into a patient's heart and at least one other lead positionable proximate to an upper airway muscle or nerve. An exemplary device may have more leads or fewer leads.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for sensing activity of and/or stimulation of autonomic nerves, non-myocardial tissue, other nerves, etc. For example, this lead may be positioned in and/or near a patient's heart or near an autonomic nerve within a patient's body and remote from the heart. Various examples described herein include positioning a lead proximate to the right and/or the left carotid sinus nerve for at least purposes of sensing nerve activity.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for sensing activity of and/or stimulating autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of sensing activity of and/or stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of sensing activity of and/or stimulating an autonomic nerve, non-myocardial tissue, other nerves, etc., wherein such an electrode may be positioned on the lead or a bifurcation or leg of the lead.

Figure 2:
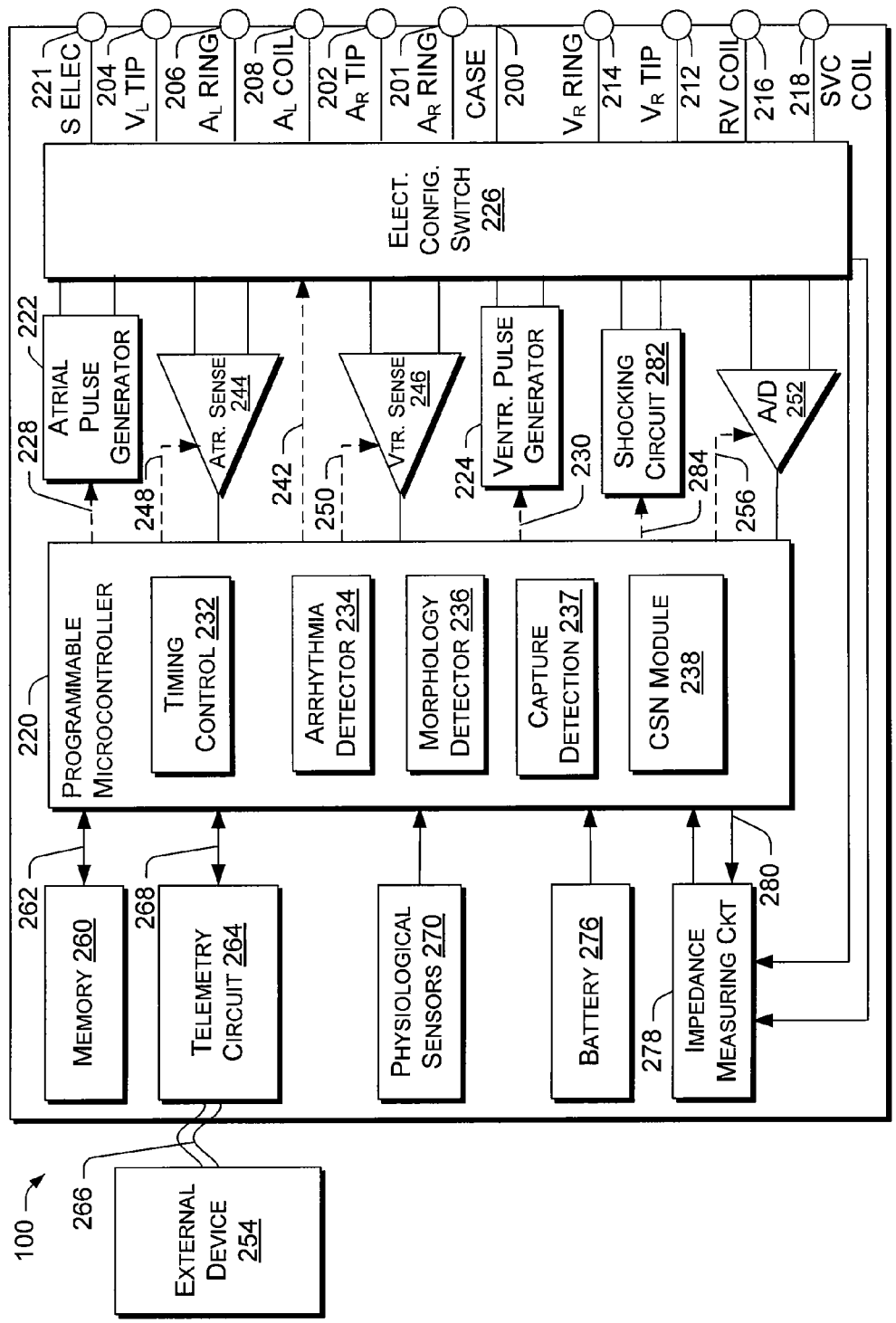
FIG. 2 is a functional block diagram of an exemplary implantable stimulation device illustrating basic elements that are configured to provide cardioversion, defibrillation, pacing stimulation or other tissue or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a CSN module 238 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The CSN module 238 may perform a variety of tasks related to, for example, arterial blood chemical composition and/or arterial blood pressure. This component can be utilized by the stimulation device 100 in determining therapy in response to chemosensory and/or barosensory information. The CSN module 238 may be implemented in hardware as part of the microcontroller 220, or as software/firmware instructions programmed into the device and executed on the microcontroller 220 during certain modes of operation. The CSN module 238 may optionally implement various exemplary methods described herein. The CSN module 238 may interact with the physiological sensors 270, the impedance measuring circuit 278 and optionally other modules. One or more of the physiological sensors 270 are optionally external to a pulse generator yet can provide information to the microcontroller 220.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (ND) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals and/or other signals across any pair of desired electrodes. The data acquisition system 252 is optionally configured to sense nerve activity and/or muscle activity from muscles other than the heart.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include or communicate with one or more physiologic sensors 270. The physiologic sensors 270 may be housed within the case 200, on the surface of the case 200 or external to the case 200. The one or more physiologic sensors optionally connect to the device 100 via one or more of the connectors or via other connectors. In some instances, a physiologic sensor may communicate with the microcontroller 220 via a wireless link. For example, a wristwatch physiologic sensor may communicate via electromagnetic radiation signals or other signals with a circuit in the device 100 (e.g., the telemetry circuit 264). Of course, an implantable physiologic sensor may also communicate with the device 100 via such communication means.

A physiologic sensor may be used to implement "rate-responsive" therapy where information sensed is used to adjust pacing stimulation rate according to, for example, the exercise state of the patient. A physiological sensor may be used to sense changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). The microcontroller 220 can respond to such information by adjusting any of the various pacing parameters (e.g., rate, AV Delay, V-V Delay, etc.) or anti-arrhythmia therapy parameters (e.g., timing, energy, leading edge voltage, etc.).

The exemplary device 100 optionally includes a connector capable of connecting a lead that includes a pressure sensor. For example, the connector 221 optionally connects to a pressure sensor capable of receiving information pertaining to chamber pressures or other pressures. Pressures may be related to cardiac performance and/or respiration. Pressure information is optionally processed or analyzed by the CSN module 238.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., airway, lung, thoracic, chamber of heart, vessel, etc.).

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electro-mechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 $mm^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Anatomy of Carotid Body and Sinus

Various exemplary techniques described herein relate to the carotid body and the carotid sinus. The carotid body is a small cluster of chemoreceptors and supporting cells located near the bifurcation of the carotid artery. It responds to changes in the composition of arterial blood, including the partial pressures of oxygen and carbon dioxide as well as pH, temperature and potassium concentration. The chemoreceptors responsible for sensing changes in blood gasses are called glomus cells. The carotid body is involved in both respiratory and cardiovascular control through complex neural pathways, for example, the carotid body provides for a reflex adjustment of respiration according to arterial blood chemistry. Hypoxia (decrease in $PO_2$), hypercapnia (increase in $PCO_2$), and acidosis (decrease in pH) increase the rate of chemosensory discharges in the carotid sinus nerve (CSN) and initiate ventilatory and cardiovascular reflex adjustments.

More specifically, the carotid body responds to a decrease in $PaO_2$ (e.g., atrial hypoxia), ischemia (e.g., from hypotension), an increase in $PCO_2$ (e.g., >10 mmHg), a decrease in pH (e.g., >about 0.1 to about 0.2 pH units), metabolic poisons (e.g., cyanide), drugs (e.g., nicotine, lobeline) and a decrease in blood glucose concentration.

While mechanisms underlying communication between glomus cells of the carotid body and petrosal ganglion neurons are not completely known, glomus cells, in response to natural and pharmacological stimuli, are expected to release at least one excitatory transmitter that generates discharges in the sensory nerve terminals of petrosal ganglion (PG) neurons.

The carotid sinus is a small oval bulge at the commencement of the internal carotid artery. At the carotid sinus, the arterial wall is thin and has a rich nerve supply from CN IX as well as some innervation from CN X. These nerves form an afferent limb of baroreceptor reflex changes in heart rate and blood pressure.

The regulation of arterial blood pressure involves negative feedback systems incorporating baroreceptors located in the carotid sinus and in the aortic arch. The carotid sinus nerve (CSN) branch of CN IX innervates the carotid sinus, which synapses in the brainstem. The aortic arch baroreceptors are innervated by the aortic nerve, which then combines with the vagus nerve (X cranial nerve) traveling to the brainstem. Arterial baroreceptors are sensitive to stretching of the walls of the vessels in which the nerve endings lie. Increased stretching augments the firing rate of the receptors and nerves, and recruits additional afferent nerves. The receptors of the carotid sinus respond to pressures ranging from about 60 mm Hg to about 180 mmHg.

Exemplary Arrangement and Method

Figure 3:
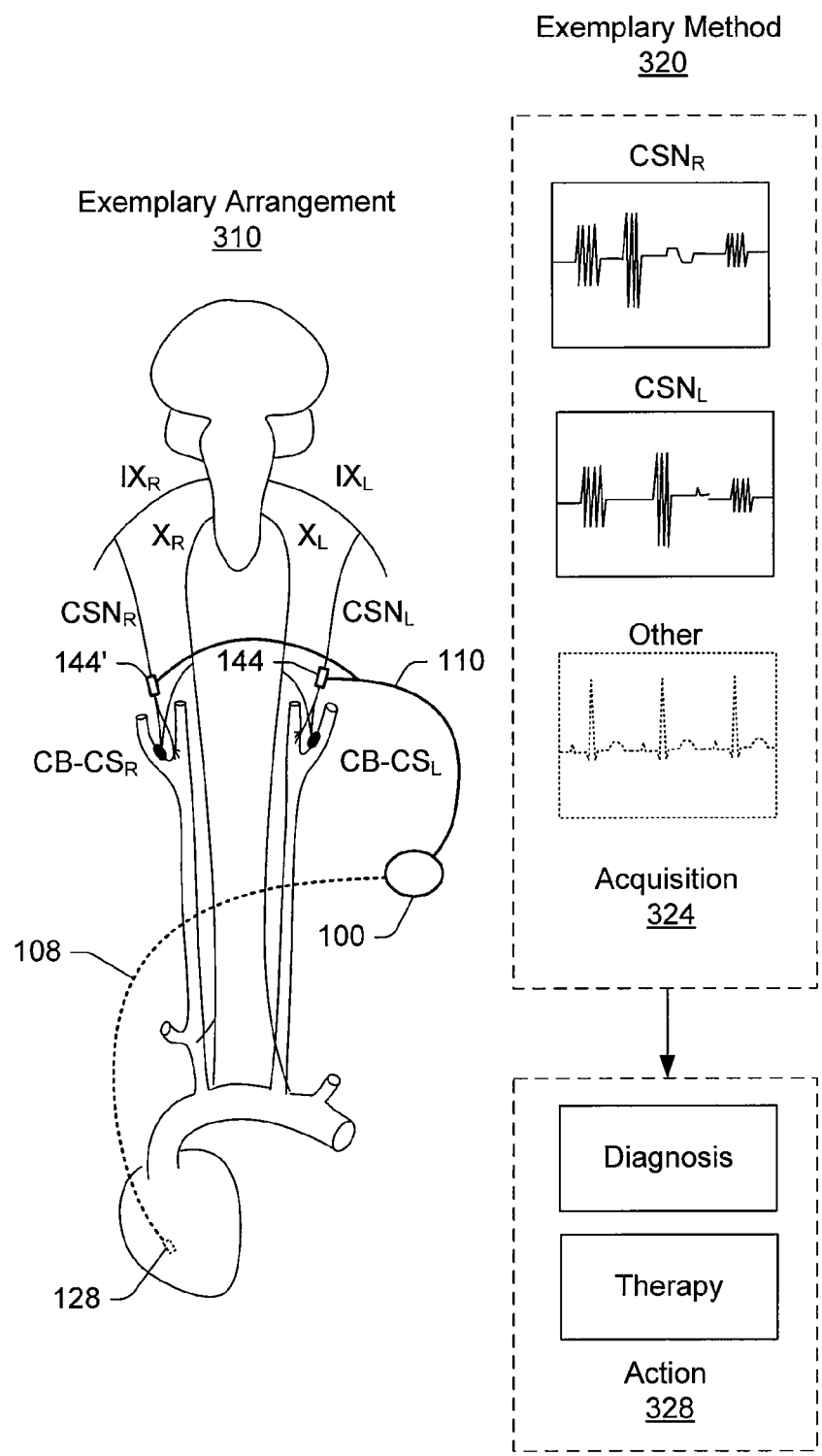
FIG. 3 is an approximate anatomic diagram that includes the right and left carotid body and sinus and an exemplary method for acquiring nerve information.

FIG. 3 shows an exemplary arrangement 310 and an exemplary method 320 for acquiring nerve information and acting based at least in part on the acquired nerve information. The arrangement 310 is shown with reference to the heart, the brain, the aorta, the right common carotid artery and bifurcation, the left common carotid artery and bifurcation, the right carotid body and sinus ($CB\text{-}CS_R$), the left carotid body and sinus ($CB\text{-}CS_L$), and the ninth and tenth cranial nerves. The carotid arteries carry blood to the brain and innervation of the carotid body and sinus, which are located near the brain, allow the body to monitor blood flow and blood chemistry and respond accordingly. The tenth cranial nerve (CN X) is the vagus nerve and is primarily associated with parasympathetic activity. The vagus includes the right vagus ($X_R$) and the left vagus ($X_L$). Various studies indicate that the vagus may innervate the carotid body while vagal innervation of the aortic baroreceptors is well established.

The arrangement 310 includes the implantable device 100 and an implantable lead 110. The lead 110 includes one or more electrodes 144, 144' and may include a bifurcation that allows at least one electrode to be positioned at, or proximate to, each CSN. In the example of FIG. 3, the lead 110 includes a bifurcation where one branch of the lead allows for positioning the electrode 144' at the right CSN ($CSN_R$) and another branch of the lead allows for positioning the electrode 144 at the left CSN ($CSN_L$).

The device 100 optionally includes various features of the device 100 of FIGS. 1 and 2. For example, a lead 108 that includes an electrode 128 is shown positioned in a chamber of the heart, which may be suitable for stimulation and/or acquiring information related to cardiac activity. At a minimum, the device 100 includes circuitry to acquire nerve information such as nerve activity information due to polarization/depolarization of one or more nerve fibers. An exemplary arrangement optionally includes features for acquiring vagal nerve information and glossopharyngeal nerve information.

The exemplary method 320, which may use the arrangement 310, includes acquiring information 324 and acting based at least in part on the acquired information 326. The acquired information may include information from the right CSN and/or the left CSN and optionally one or more other types of information such as cardiac information, respiratory information, etc. The action 328 may include diagnostic action or therapeutic action.

Detailed Anatomy

Figure 4:
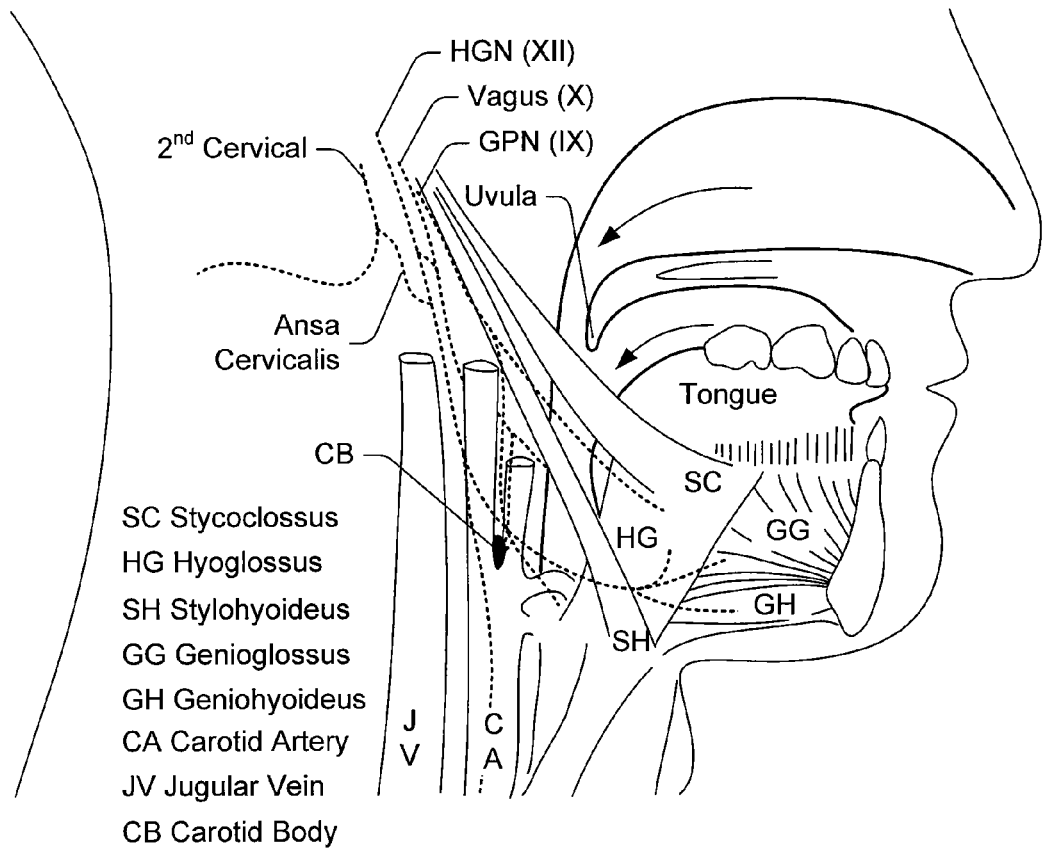
FIG. 4 is an approximate anatomical diagram related to anatomy of the right cervical region and pathways from the carotid body and sinus to the solitary nucleus.
Figure 4:
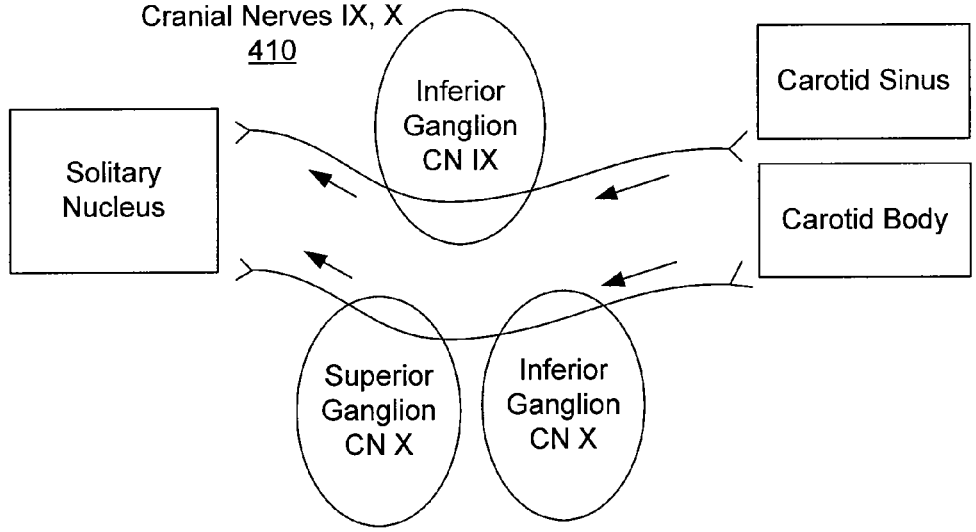

FIG. 4 is an anatomical diagram 400 and a block diagram 410 that illustrate approximate positions of CN IX and CN X as well as communication pathways to the solitary nucleus of the brain. CN IX emerges behind the olive and exits the jugular foramen where it shows two unipolar-cell ganglia and gives off a tympanic branch which is partly sensory to the middle ear, partly parasympathetic to the parotid gland via the otic ganglion. CN IX then passes between superior and middle constrictors to gain the oropharynx, where it supplies sensation to that mucous membrane including the posterior third of tongue (hence the name), and taste fibers to the circumvallate papillae.

As already mentioned, a branch of CN IX innervates baroreceptors of the carotid sinus and chemoreceptors of the carotid body. This branch includes two sets of afferent fibers. One set ramifies in the wall of the carotid sinus (at the commencement of the internal carotid artery), terminating in stretch receptors responsive to systolic blood pressure; these baroreceptor neurons terminate centrally in the medial part of the nucleus solitarius. The second set of afferents in the carotid branch supplies glomus cells in the carotid body. These nerve endings are chemoreceptors monitoring blood chemistry. The central terminals enter the dorsal respiratory nucleus. More generally, the nerve supply to the carotid sinus and body is derived from the carotid branch of CN IX, branches to the carotid body from the inferior ganglion of CN X and sympathetic branches from the superior cervical ganglion.

Afferent nerve activity of CN IX due to a change in blood pressure, a decrease in blood oxygen concentration, a decrease in blood pH, and/or an increase in blood carbon dioxide concentration can cause corrective changes in ventilation so as to maintain blood gas and pH homeostasis.

Figure 5:
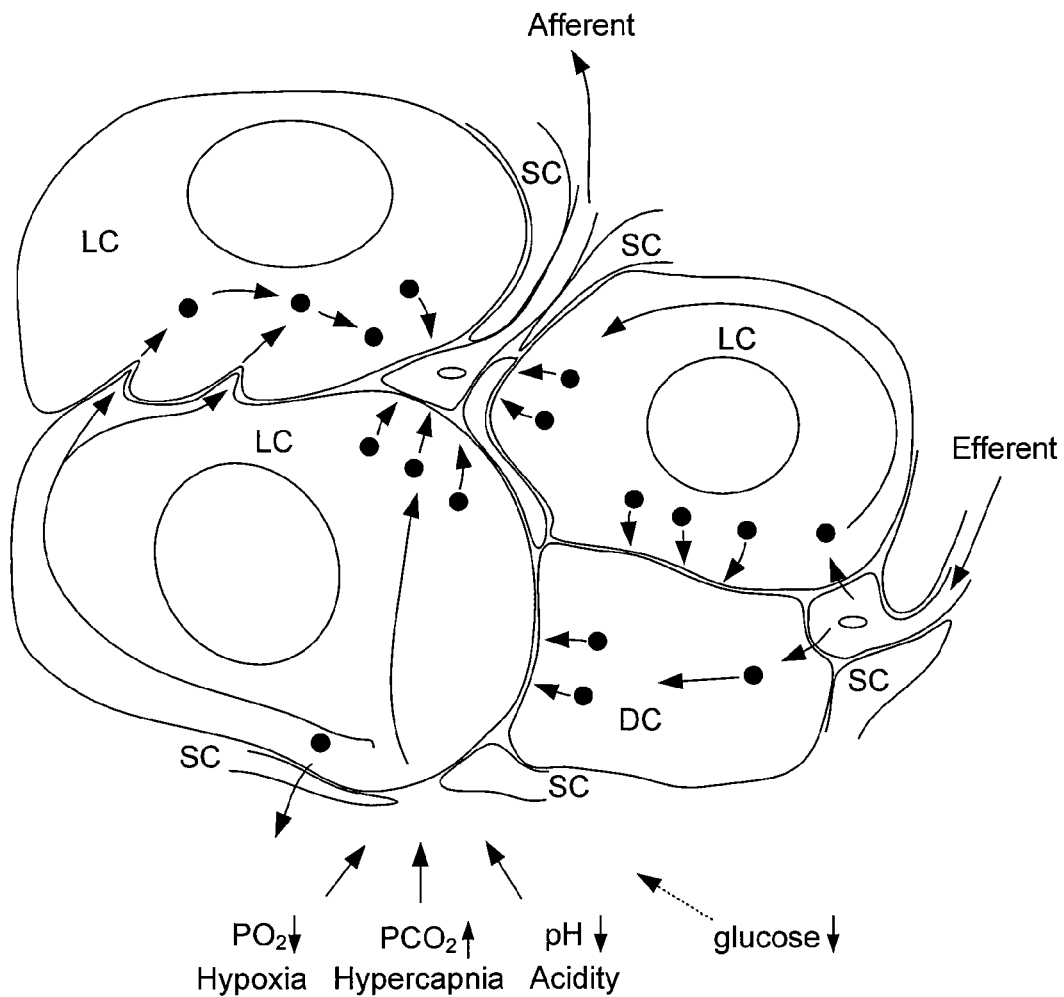
FIG. 5 is an approximate anatomical diagram of a unit of the carotid body responsive to chemical changes.
Figure 5:
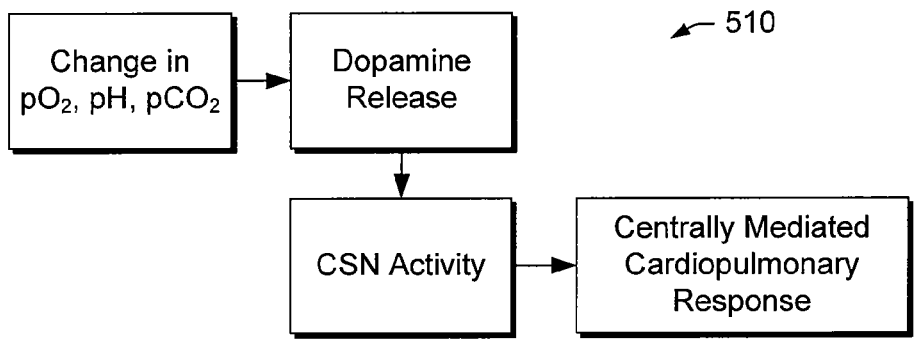

FIG. 5 shows a more detailed diagram of a cell unit of the carotid body 500 and a block diagram of a process 510. Sustentacular cells (modified Schwann cells, labeled SC) are intimately surrounded and interlaced with a rich network of capillaries and venules. Clusters of cells are called "zellballen", and can generally be separated into "light" cell (labeled LC) and "dark" cell (labeled DC) subpopulations, referring to the density of intracellular neurosecretory granules. Chief cells are members of the amine precursor and uptake decarboxylase (APUD) family, recently referred to as the DNES (diffuse neuroendocrine system). The term glomus was applied originally because it was erroneously thought that the chief cells arose from specialized pericytes as seen in true arteriovenous complexes ("glomus complexes"); noting that the term glomus is still commonly used.

A cell unit of a carotid body generates afferent nerve activity responsive to blood chemistry. For example, in the process 510, a decrease in oxygen concentration, a decrease in pH and/or an increase in carbon dioxide can cause cells of the unit to release dopamine, which increases CSN activity and provokes centrally-mediated cardiopulmonary responses. While various examples discuss afferent nerve activity, some studies indicate that the carotid body includes efferent innervation, which may be via the CSN. Thus, various exemplary techniques may include acquiring efferent nerve information (e.g., via sensing, filtering, analyzing, etc.).

Exemplary Methods and Arrangements

Figure 6:
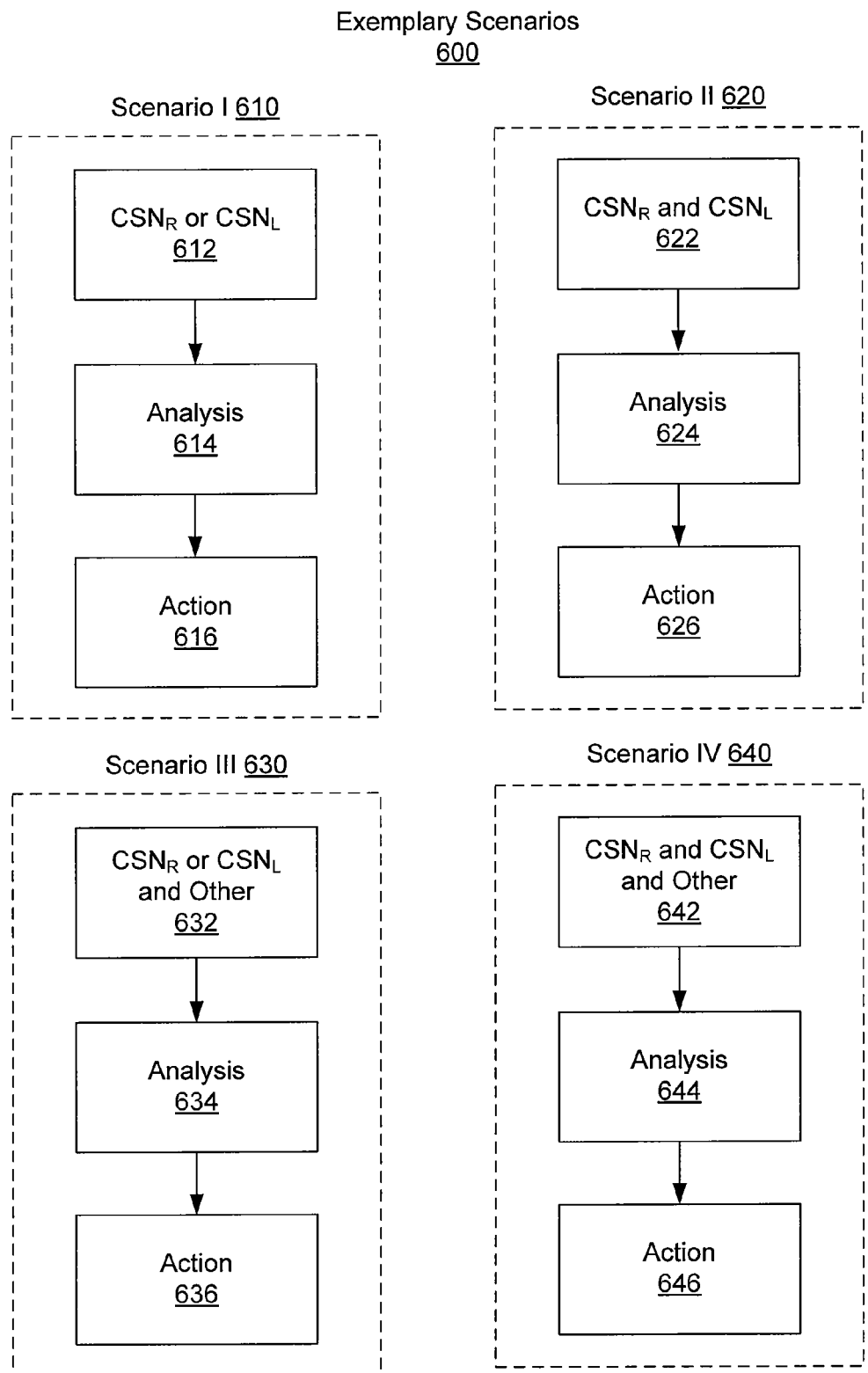
FIG. 6 is a block diagram of various exemplary scenarios for acquiring nerve information, analyzing the information, and acting on the information.

FIG. 6 shows exemplary scenarios 600 for acquiring nerve information, analyzing such information and acting based at least in part on the acquired information and/or the analysis thereof. Scenario I 610 includes an acquisition block 612 that acquires nerve information from $CSN_R$ or $CSN_L$. The acquisition may occur via use of one or more electrodes capable of sensing nerve activity (e.g., cuff electrodes, etc.). For example, an implantable device may include one or more cuff or plate electrodes that can be placed around, in, and/or on the nerve with or without an anchoring mechanism to avoid dislodgment.

An analysis block 614 analyzes acquired nerve information. For example, an analysis block 614 may include one or more filters (e.g., high pass, low pass, band pass, etc.), a recognition algorithm, a Bayesian or neural network algorithm, etc., that can determine if the acquired nerve information indicates a change in physiologic condition (e.g., a change in blood pressure and/or blood chemistry).

An action block 616 may act on nerve information and/or an analysis of nerve information. For example, if a nerve signal amplitude or frequency exceeds a certain limit associated with blood pressure, then the action block 616 may call for an adjustment to a therapy such as a cardiac pacing therapy to control blood pressure. Where indicia of a change in physiology are not amenable to a simple limit approach, then an analysis may be used to determine whether a change has occurred in one or more physiological conditions. The analysis block 614 may perform such an analysis and then instruct the action block 616 to take appropriate action.

Scenario II 620 includes an acquisition block 622 that acquires nerve information from both $CSN_R$ and $CSN_L$. In scenario II 620, an analysis block 624 may use a differential approach. For example, certain physiological conditions may be indicated by a difference in nerve activity at $CSN_R$ and $CSN_L$. An analysis may simply subtract a $CSN_R$ electroneurogram from a $CSN_L$ electroneurogram. Alternatively, a sensing arrangement may provide for acquisition of a differential signal (e.g., using a common electrode or common acquisition circuitry). Referring to FIG. 3, a small time differential may exist between a bolus of blood exiting the left ventricle and a portion of the bolus reaching the right carotid body and a portion of the bolus reaching the left carotid body. Such a time difference ($\Delta t$) may be used in synchronizing nerve activity with blood exiting the left ventricle. For example, if a decrease in blood oxygen causes an increase in nerve activity at $CSN_R$ at time $t_1$ then an increase in nerve activity at $CSN_L$ may be expected to occur at time $t_1 + \Delta t$.

The action block 626 of scenario II 620 may act on nerve information and/or an analysis of nerve information. For example, if a delay between $CSN_R$ and $CSN_L$ changes or exceeds a limit, then the action block 626 may issue an alert to a patient or a care provider. In all of the scenarios of FIG. 6, an action may simply store information for analysis or review at a later time (e.g., by an implantable device and/or an external device).

Scenario III 630 includes an acquisition block 632 that acquires $CSN_R$ or $CSN_L$ information and other information. Other information may be cardiac activity information, patient activity information, patient position information, respiratory information, autonomic nerve information, etc. In scenario III 630, the analysis block 634 may use the nerve information to confirm or assess the other information. For example, where the other information is acquired using a pressure sensor for sensing blood pressure, the nerve information may be used to confirm a change in blood pressure. In another example, photoplethysmography may be used to sense blood gas levels and nerve information may be used to confirm such levels. In yet another example, impedance plethysmography may be used to monitor changes in blood volume (or edema) and nerve information may be used to assess consequences of a change in blood volume.

The action block 636 may initiate an action based on an analysis that uses nerve information to confirm or assess other information. The action block 636 may store information, results of an analysis and/or call for therapeutic action.

The scenario IV 640 includes an acquisition block 642 that acquires $CSN_R$, $CSN_L$ and other information. For example, the other information may be CN $X_R$ and CN $X_L$ nerve information acquired using the same implantable system used to acquire the $CSN_R$ and $CSN_L$ information. The analysis block 644 may analyze such information in any of a variety of manners to allow an action block 646 to take appropriate action. Referring again to FIG. 3, branches of the vagal nerve ($X_R$ and $X_L$) innervate the baroreceptors of the aortic arch. Information acquired from these branches may be used in conjunction with information from $CSN_R$ and $CSN_L$ to assess arterial blood pressure. Given the implantable device 100, such an assessment may be used to adjust a cardiac pacing therapy to control blood pressure. Information may be acquired during or after control to provide a feedback loop that optionally enhances the cardiac pacing therapy's ability to control blood pressure.

Figure 7:
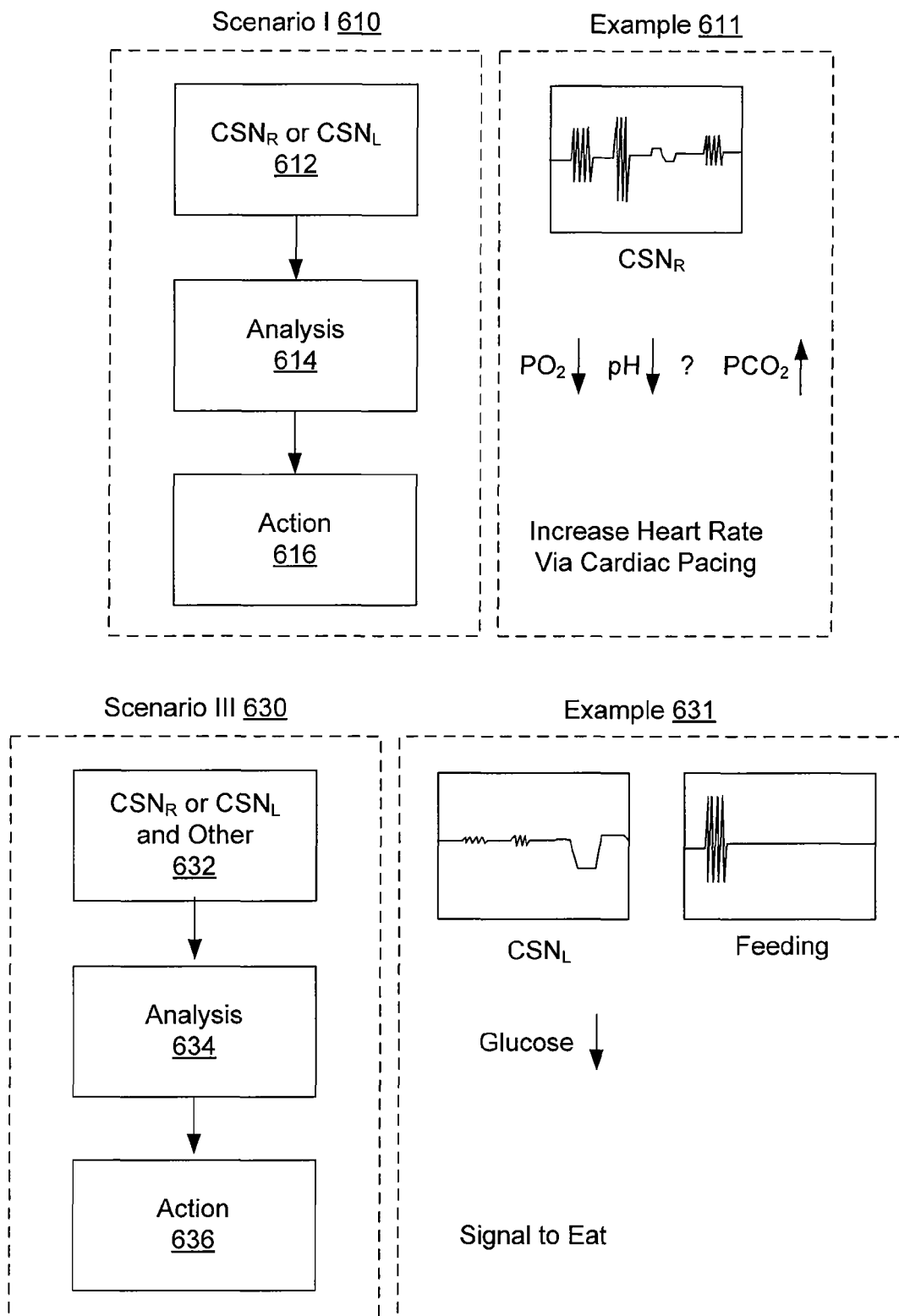
FIG. 7 is a block diagram of scenarios I and III of FIG. 6.

FIG. 7 shows an example 611 using scenario 1610 and an example 631 using scenario III 630. In the example 611 for scenario 1610, the acquisition block 612 acquires an electroneurogram of $CSN_R$ activity. The analysis block 614 analyzes the electroneurogram and determines that blood oxygen concentration and pH decreased while blood carbon dioxide concentration increased. The analysis also determines that certain nerve information cannot be readily identified or associated with a change in physiological condition (see "?" in FIG. 7). Based at least in part on the analysis, the action block 616 instructs an implantable cardiac pacing device to increase heart rate.

In the example 631 for scenario III 630, the acquisition block 632 acquires $CSN_L$ nerve activity and activity from a feeding sensor. In this example, the analysis block 634 determines that the $CSN_L$ nerve activity indicates a low blood glucose concentration and that feeding has not occurred for about 6 hours (noting that the scales on the $CSN_L$ plot and feeding plot may differ). In response, the action block 636 calls for issuance of an alert to commence feeding due to low blood glucose concentration.

Figure 8:
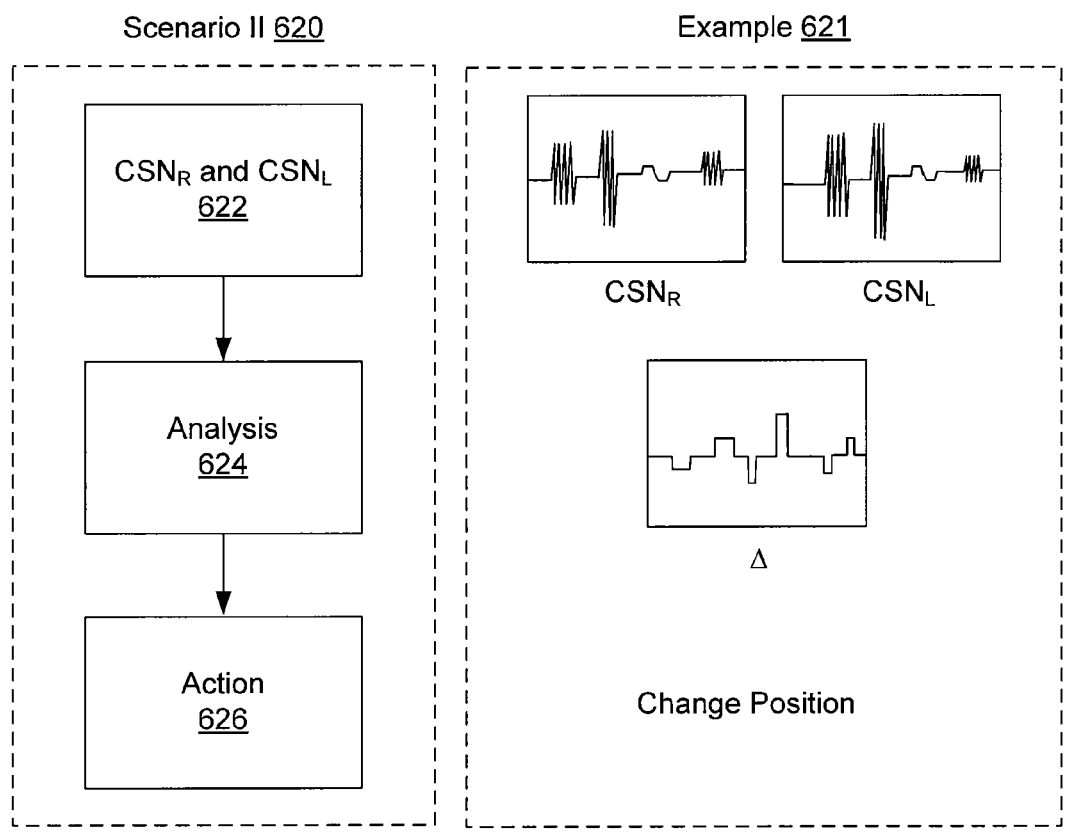
FIG. 8 is a block diagram of scenario II of FIG. 6.

FIG. 8 shows an example 621 for scenario II 620 of FIG. 6. In this example, the acquisition block 622 acquires nerve information for both $CSN_R$ and $CSN_L$. The analysis block 624 determines a differential based on the acquired nerve information. In turn, the action block 626 issues an alert to instruct a patient to change body position. For example, a delay between right side and left side nerve information may indicate an imbalance in blood flow. To compensate for the imbalance, an exemplary device may vibrate or deliver a stimulus (e.g., at a certain frequency) that notifies a patient to change body position to thereby balance blood flow. In general, the heart experiences more force when a patient lies on her left side compared to lying on her right side. Such force may cause an imbalance in blood flow (e.g., pressure) in the carotid arteries, the degree of which can be determined using $CSN_R$ and $CSN_L$ activity information.

With respect to the differential, a plot labeled "A" demonstrates a delay in nerve activity where right side activity commences earlier than left side activity and where left side activity persists after right side activity terminates. Amplitudes, morphology, frequencies, etc., may be used to determine a differential suitable for diagnostic or therapeutic action.

Figure 9:
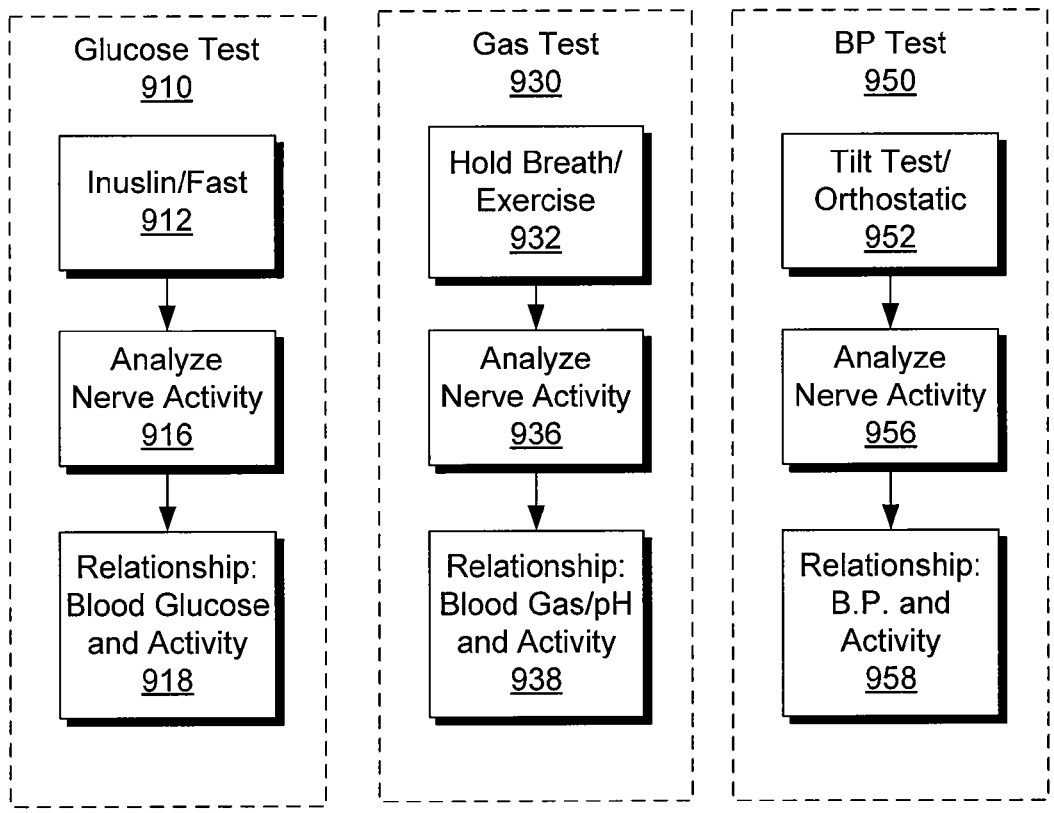
FIG. 9 is a series of block diagrams for various exemplary methods and arrangements for implementing methods that can facilitate analysis of nerve activity.
Figure 9:
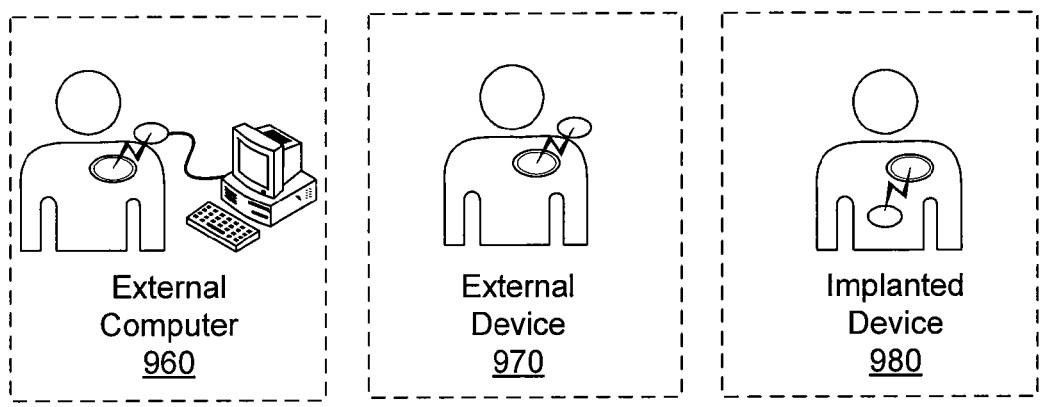

FIG. 9 shows various exemplary methods and arrangements of equipment 900. The methods 910, 930, 950 are suitable for associating nerve activity with a physiological condition. Various exemplary arrangements or systems are shown with respect to an implantable device capable of acquiring CSN information 960, 970, 980.

The glucose test method 910 establishes a relationship between nerve activity and blood glucose concentration. An administration block 912 causes a patient's blood glucose concentration to decrease. For example, a care provider or patient may administer an injection of insulin, an anabolic hormone that controls cellular intake of certain substances, most prominently glucose in muscle and adipose tissue, as well as glycogen synthesis, glycogen storage in liver and muscle cells, fatty acid synthesis in fat cells, increase potassium uptake among other effects. Overall, an increase in CSN activity or a change in CSN activity may be expected in response to an insulin induced decrease in blood glucose concentration (hypoglycemia). Fasting may achieve a similar decrease, especially for a diabetic patient. Further, the method 910 may include administration of a catabolic hormone or a carbohydrate to increase blood glucose concentration. Using such techniques, an analysis block 916 may analyze a certain portion of an electroneurogram (e.g., marked by administration of two opposing treatments) to establish a relationship between blood glucose concentration and CSN activity, per block 918.

An exemplary method may use the relationship between blood glucose concentration and CSN activity to control therapy. For example, an implantable device may detect hypoglycemia and issue a signal for a patient or care provider to take appropriate action (see, e.g., arrangements 960, 970, 980). Where a patient has an implanted insulin pump that delivers insulin according to a schedule or zero-order basis, detection of hypoglycemia may cause the pump to cease delivery of insulin (see, e.g., arrangement 980). For example, some pumps deliver a basal dose on an approximately zero-order basis (e.g., substantially constant basis). CSN information may be used to adjust such delivery. In instances where a glucometer is used, CSN information may be used to confirm or assess a glucometer reading. Some glucometers include circuitry for wireless communication with an implanted insulin pump. CSN information may be acquired by an implanted insulin pump or otherwise communicated to an implanted insulin pump or an external device such as a glucometer (see, e.g., arrangements 970, 980).

While the above examples mention use of a glucometer in conjunction with nerve information, an accelerometer or other sensor capable of detecting steadiness or patient activity may be used additionally or alternatively to determine if a patient is dizzy, losing consciousness, etc. (see, e.g., arrangement 980, device 100 of FIGS. 1 and 2).

Other types of therapy related to blood glucose or insulin concentration may include activation or blocking of one or more autonomic nerves related to pancreatic activity (e.g., pancreatic vagal stimulation).

The gas test method 930 establishes a relationship between nerve activity and blood gas(es) concentration(s) and optionally blood pH (hydrogen ion concentration). An administration block 932 causes a patient's blood oxygen level to decrease and blood carbon dioxide level to increase. For example, patient may hold her breath or exercise to cause such changes in blood gas concentrations. After or before such administration, a patient or a care provider may administer oxygen (e.g., oxygen mask or positive pressure mask) to the patient to increase the blood oxygen concentration. Using such techniques, an analysis block 936 may analyze a certain portion of an electroneurogram (e.g., marked by administration of two opposing treatments) to establish a relationship between blood gas(es) concentration(s) and CSN activity, per block 938. Such a relationship or relationships may be used in detection or treatment of respiratory disorders such as apnea, which is discussed further below.

The blood pressure test method 950 establishes a relationship between nerve activity and blood pressure. An administration block 952 administers a tilt test or other test that causes a patient's blood pressure to change. Using such techniques, an analysis block 956 may analyze a certain portion of an electroneurogram (e.g., marked by administration of two opposing states) to establish a relationship between blood pressure and CSN activity, per block 958. Such a relationship or relationships may be used in detection or treatment of various conditions including cardiopulmonary (e.g., congestive heart failure) and respiratory disorders (e.g., apnea, which is discussed below).

Apnea includes central sleep apnea (CSA) and obstructive sleep apnea (OSA). During obstructive apneas, chemoreflex activation by hypoxemia (low $PO_2$) and hypercapnia (high $PCO_2$) can cause even further increases in sympathetic activity, with recurrent surges in blood pressure most notable at the end of apneic events. Blood pressure may increase up to 250/130 mm Hg even though the patient is normotensive during wakefulness (see, e.g., Somers et al., "Sympathetic neural mechanisms in obstructive sleep apnea". *J Clin Invest*. 1995; 96:1897-1904).

Patients treated with continuous positive airway pressure (CPAP, which increases $PO_2$) after apneic events demonstrate attenuation of the increase in sympathetic nervous system activity while patients with untreated OSA have higher sympathetic nervous system activity compared with controls, even when awake and normoxic. Patients with untreated OSA also have faster heart rates, blunted heart rate variability, and increased blood pressure variability during normoxic daytime wakefulness.

As described herein, the blood gas test method 930 and/or the blood pressure test method 950 may be used in treatment of apnea. For example, the gas test method 930 and/or the blood pressure test method 950 may be performed and resulting relationships used for administering anti-apnea therapy and/or apnea breaking therapy. An anti-apnea therapy may respond to nerve activity indicative of decreasing $PO_2$ or increasing $PCO_2$ while an apnea breaking therapy may respond to nerve activity indicative of a change in blood pressure. An exemplary method may use both approaches and optionally include use of other information to call for or adjust an apnea therapy. An apnea therapy may include delivery of stimulation to tissue or other action (e.g., vibration, etc.). Apnea therapies that stimulate tissue may stimulate one or more of the myocardium, the phrenic nerve, the diaphragm, the upper air muscles, etc.

The exemplary arrangement 970 may include an implantable device that acquires CSN information and that communicates with an external device for delivery of an apnea therapy (e.g., a positive airway pressure device). The exemplary arrangement 980 may include an implantable device that acquires CSN information and that communicates with another implantable device for delivery of an apnea therapy (e.g., a phrenic nerve stimulation device).

With respect to OSA, maintenance of upper airway patency ultimately depends on a balance between stabilizing and collapsing forces. Factors involved in effective stabilization of upper airway structures include upper airway neuromuscular activity, physiological properties of upper airway muscles, effectiveness of upper airway muscle contraction and mechanical coupling of upper airway muscles to surrounding soft tissues.

Phasic activity of upper airway muscles is known to precede that of respiratory muscles in normal patients as well as those affected by OSA. The contraction of upper airway dilators generates the only stabilizing force that opposes a series of collapsing forces, including the effects of gravity-induced posterior displacement of upper airway structures, the negative inspiratory upper airway transmural pressure gradient, and surface tension forces. Maintenance or alteration of upper airway patency may consider contraction of dilators as well as characteristics of the collapsing forces. As the right and left CSN are located proximate to the upper airway, an exemplary device may acquire CSN information and optionally other information and deliver an apnea therapy that includes stimulation of a nerve or tissue to promote upper airway patency.

As described herein, sensing of nerve activity, sensing of muscle activity, delivery of energy to one or more nerves and/or delivery of energy to one or more muscles may be used to maintain upper airway patency. Referring to FIG. 4, the upper airway anatomy is shown along with pathways of CN IX, CN X and CN XII. An exemplary method may acquire information from one or more of these nerves. Such information may be used in conjunction with an apnea treatment therapy (e.g., prevention, breaking or recovery).

With respect to respiration or autonomic tone, which may be considered other information for use in conjunction with CSN information, an implantable device may include features for measuring respiratory sinus arrhythmia (RSA). RSA is a natural cycle of arrhythmia that occurs through the influence of breathing on autonomic tone. During inspiration vagus nerve activity is impeded, which shifts the autonomic tone towards sympathetic. In response, the RR interval shortens, i.e., heart rate increases. During expiration, the autonomic tone shifts toward parasympathetic and the RR interval lengthens, i.e., heart rate decreases. While research indicates that both parasympathetic and sympathetic mechanisms contribute to RSA, RSA is primarily due to changes in parasympathetic activity.

As described herein, sensing heart rate or RR interval may be used to determine one or more respiratory characteristics. Further, sensing heart rate or RR interval may be used to estimate autonomic tone or other autonomic characteristic. For example, if there is little change in heart rate over one or more respiratory cycles, then the autonomic tone may be shifted toward sympathetic. Yet further, excessive RSA may indicate an overactive parasympathetic system.

As already mentioned, the CSN responds to potassium concentration. An exemplary method may include administration potassium (e.g., salt solution) to excite the CSN. Further, administration of potassium may be used to enhance CSN activity caused by hypoxia. Acquisition and analysis of nerve activity may be used to associate such activity with blood potassium concentration. A relationship between CSN activity and blood potassium concentration may be used to diagnose renal condition and/or for delivery of a renal therapy.

Figure 10:
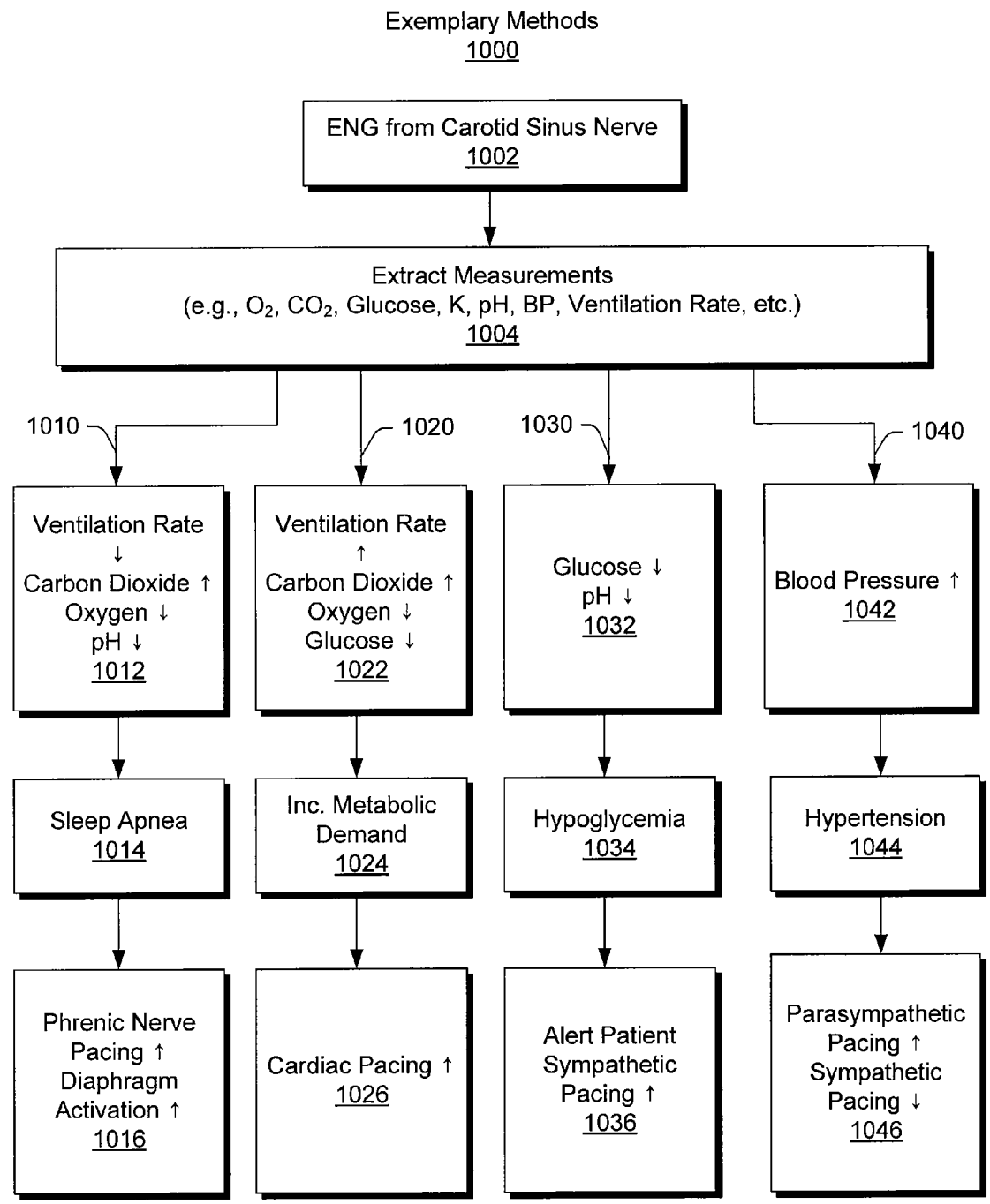
FIG. 10 is a block diagram of various exemplary methods for diagnosing conditions and optional control actions based at least in part on a diagnosis.

FIG. 10 shows a block diagram of various exemplary methods 1000 suitable for use in an exemplary implantable device that can acquire CSN information. In an acquisition block 1002, an implantable device acquires one or more electroneurograms (ENGs) from the right and/or left CSN. In an extraction or analysis block 1004, specific measurements are extracted from the one or more electroneurograms. The device may be configured to sense such information or to acquire such information from another device. The extracted measurements may include blood gas (e.g., oxygen, carbon dioxide), ion concentrations (e.g., $K^+$, $Na^+$, $H^+$), blood pressure, ventilation rate or other measurements. An implantable device may be configured to extract such measurements from one or more electroneurograms or to acquire extracted measurements from another device. In the latter instance, the other device may decide which extracted measurements to communicate.

According to the diagram 1000, measurements of the oxygen, carbon dioxide, glucose, potassium, pH, blood pressure, and ventilation rate are extracted from one or more electroneurograms of the right and/or left CSN. Based at least in part on one or more of these measurements, an implantable device may detect episodes of different physiological states and treat an episode with an appropriate therapeutic response.

An exemplary implantable device may include any of the features of the device 100 of FIGS. 1 and 2 and may be a pacemaker, a defibrillator, or a defibrillator and a pacemaker. As shown in FIG. 2, the device 100 includes a specialized processing unit (module 238) that can utilize information extracted from the right and/or left CSN, for example, to maintain homeostasis of a patient. As already described, the device 100 may be capable of controlling a variety of pacing electrodes and/or devices to change cardiac pacing, phrenic nerve pacing, parasympathetic nervous system pacing, and/or sympathetic nervous system pacing. The device 100 may also include circuitry to alert a patient about events. In general, the device 100 includes memory capable of storing information where a care provider or patient may retrieve the information.

The module 238 may include an algorithm to process nerve information using techniques such as analog filters, digital filters, digital signal processing, and/or classification algorithms (e.g., neural networks, genetic algorithms, wavelet decomposition, Bayesian classifiers, and kth nearest neighbor).

An exemplary device may use electrical activity of the right and/or left CSN associated with ventilation rate, oxygen concentration, carbon dioxide concentration, potassium concentration, glucose concentration, blood pressure, pH, etc., to detect episodes of sleep apnea (low ventilation, low oxygen, and high carbon dioxide), increased/decreased levels of metabolic demand (high ventilation, low oxygen, and high carbon dioxide), episodes of hypoglycemia (co-morbidity of cardiovascular disease), hypertension, and other episodes such as hyperkalemia, acidemia, hypoxia, and hypercapnia.

An exemplary implantable device may use one or more extracted measurements for any of a variety of purposes. In the example of FIG. 10, four exemplary methods 1010, 1020, 1030 and 1040 are shown that may be implemented by an implantable device configured to call for various actions and optionally perform such actions.

Sleep apnea, as discussed above, a co-morbidity of heart failure, can lead to neurocognitive deficits, daytime fatigue, pauses in breathing, arterial oxygen desaturation, and cardiovascular consequences such as hypertension and stroke. Sleep apnea causes a decrease in ventilation rate, oxygen concentration, and pH, and an increase in carbon dioxide concentration.

The exemplary method 1010 can diagnose and treat sleep apnea. In a measurement analysis block 1012, the method 1010 can, for example, determine trends based on extracted measures. In turn, a diagnosis block 1014 uses the analyzed information to diagnose patient condition. In this example, a decrease in ventilation rate, an increase in carbon dioxide concentration, a decrease in oxygen concentration and a decrease in blood pH are indicative of sleep apnea. The diagnosis can then be used to call for appropriate therapeutic action per an action block 1016. For example, phrenic nerve stimulation, diaphragm activation, or other action may counter sleep apnea.

When combined with the acquisition block 1002 and the extraction block 1004, the exemplary method 1010 provides for diagnosing sleep apnea by acquiring an electroneurogram of carotid sinus nerve activity, analyzing the electroneurogram for at least one of a decrease in ventilation rate, an increase in blood carbon dioxide concentration, a decrease in blood oxygen concentration and a decrease in blood pH and, based at least in part on the analyzing, determining if sleep apnea exists. Such a method optionally includes, if sleep apnea exists, calling for and/or delivering a therapy to treat sleep apnea.

An exemplary implantable device includes features perform the method 1010. For example, a device may include features to detect a decrease in ventilation rate, oxygen concentration, and pH, and an increase in carbon dioxide concentration and optionally to classify this response as sleep apnea or a particular type of sleep apnea. In turn, the device may call for action to counteract the sleep apnea episode such as increase phrenic nerve pacing.

Increases in metabolic demand result in increased carbon dioxide production, increased ventilation, increased demand for oxygen and glucose, and increased heart rate. The exemplary method 1020 can diagnose and respond to an increase in metabolic demand. In a measurement analysis block 1022, the method 1020 can, for example, determine trends based on extracted measures. In turn, a diagnosis block 1024 uses the analyzed information to diagnose patient condition. In this example, an increase in ventilation rate and carbon dioxide concentration and a decrease in oxygen concentration and glucose concentration are indicative of increased metabolic demand. The diagnosis can then be used to call for appropriate therapeutic action per an action block 1026. For example, the action block 1026 may call for an increase in cardiac pacing rate.

When combined with the acquisition block 1002 and the extraction block 1004, the exemplary method 1020 provides for diagnosing an increase in metabolic demand by acquiring an electroneurogram of carotid sinus nerve activity, analyzing the electroneurogram for at least one of a decrease in ventilation rate, an increase in blood carbon dioxide concentration, a decrease in blood oxygen concentration and a decrease in blood glucose concentration and, based at least in part on the analyzing, determining if metabolic demand increased. Such a method optionally includes, if metabolic demand increased, calling for delivery and/or delivering a therapy to increase heart rate.

An exemplary implantable device includes features perform the method 1020. For example, an implantable device may detect a wider variety of metabolic demands when compared to a conventional pacemaker with a motion-based patient activity circuit. An exemplary device may acquire CSN information indicative of increased metabolic demands as a result of non-physical activity (intense concentration, stress, excitement, etc). For example, such a device may include features to measure an increase in ventilation rate, an increase in carbon dioxide concentration, a decrease in oxygen concentration, and a decrease in glucose concentration and classify this response as increased metabolic demand. In response, the device may instruct a cardiac pacemaker or cardiac pacing feature to increase cardiac pacing rate to compensate for the increased metabolic demand.

Diabetes, as discussed above, a co-morbidity of heart failure, is associated with hypertension, bradycardia, and tachycardia. Studies indicate that strict glucose regulation delays long-term complications of diabetes. Hypoglycemia is characterized by shaking, sweating, palpitations, fatigue, confusion, behavioral changes, and even unconsciousness. Some diabetics have a difficult time determining when they are having hypoglycemic episodes, which can increase the tendency to stay at hyperglycemic levels and, hence, hasten long-term complications of diabetes.

The exemplary method 1030 can diagnose and respond to hypoglycemia. In a measurement analysis block 1032, the method 1030 can, for example, determine trends based on extracted measures. In turn, a diagnosis block 1034 uses the analyzed information to diagnose patient condition. In this example, a decrease in blood glucose concentration and blood pH concentration are indicative of hypoglycemia. The diagnosis can then be used to call for appropriate therapeutic action per an action block 1036. For example, the action block 1036 may call for issuance of a patient alert signal and an increase in sympathetic activity (e.g., an increase in stimulation to a sympathetic nerve).

When combined with the acquisition block 1002 and the extraction block 1004, the exemplary method 1030 provides for diagnosing hypoglycemia by acquiring an electroneurogram of carotid sinus nerve activity, analyzing the electroneurogram for at least one of a decrease in blood glucose concentration and a decrease in blood pH and, based at least in part on the analyzing, determining if hypoglycemia exists. Such a method optionally includes, if hypoglycemia exists, issuing an alert, calling for delivery of a therapy to increase sympathetic tone and/or delivering such a therapy.

An exemplary implantable device includes features perform the method 1030. For example, an implantable device may include features to detect low glucose and pH levels, based at least in part on CSN information, and to stimulate the sympathetic nervous system to hinder insulin release and to hasten blood glucose release. Such a device may also alert a patient as to low blood glucose levels (e.g., by an audio, vibratory, stimulation, or other feedback mechanism).

Hypertension is another co-morbidity of heart failure. As a result of chronic hypertension, the heart hypertrophies to maintain cardiac output. Over time, the heart hypertrophies to a point where the size of the ventricles shrinks and cardiac output decreases.

The exemplary method 1040 can diagnose and respond to hypertension. In a measurement analysis block 1042, the method 1040 can, for example, determine trends based on extracted measures. In turn, a diagnosis block 1044 uses the analyzed information to diagnose patient condition. In this example, an increase in blood pressure is indicative of hypertension. The diagnosis can then be used to call for appropriate therapeutic action per an action block 1046. For example, the action block 1046 may call for an increase in parasympathetic activity (e.g., by a decrease in stimulation to a sympathetic nerve or by a change in sympathetic neural stimulation to block the neural pathway).

When combined with the acquisition block 1002 and the extraction block 1004, the exemplary method 1040 provides for diagnosing hypertension by acquiring an electroneurogram of carotid sinus nerve activity, analyzing the electroneurogram for at least a change in blood pressure and, based at least in part on the analyzing, determining if hypertension exists. Such a method optionally includes if hypertension exists, calling for delivery of or delivering a therapy to decrease sympathetic tone and/or calling for delivery of or delivering a therapy to increase parasympathetic tone.

An exemplary implantable device includes features perform the method 1040. For example, an implantable device may acquire CSN information and uses such information to detect high blood pressure and call for stimulation of the parasympathetic nervous system and/or block the sympathetic nervous system to reduce blood pressure.

An exemplary implantable device suitable for implementation of any of the various methods 1010, 1020, 1030, 1040 includes a processor, a lead bearing one or more electrodes positionable to sense electrical activity of the right carotid sinus nerve or the left carotid sinus nerve and control logic, operable in conjunction with the processor, to analyze the sensed electrical activity for chemosensory information or barosensory information. Such a device may include one or more electrodes that allow for sensing nerve activity in a neural pathway between the right carotid body or left carotid body and the brain. The control logic may include features to diagnose sleep apnea, diagnose an increase in metabolic demand, diagnose hypoglycemia, and/or diagnose hypertension.

Figure 11:
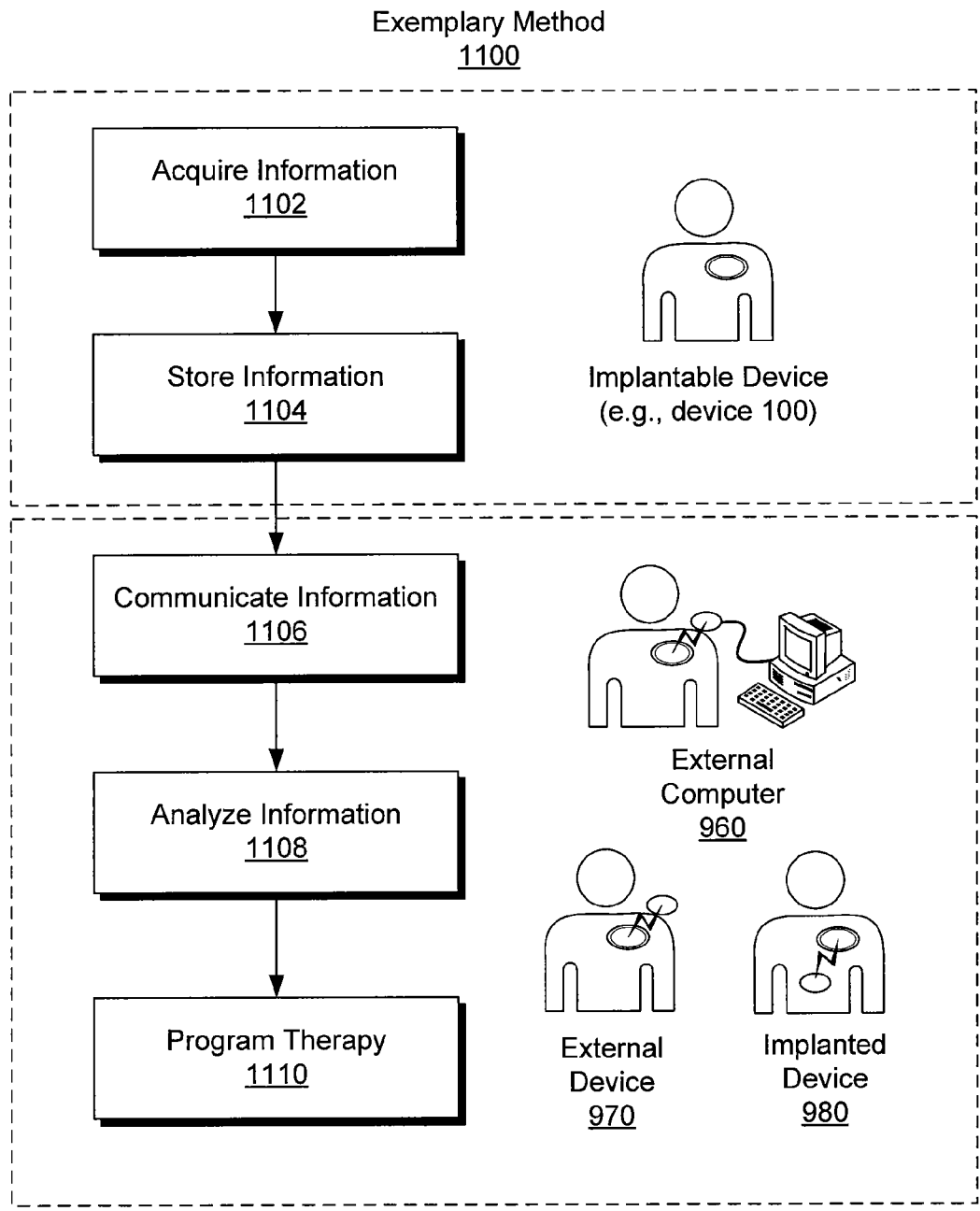
FIG. 11 is a block diagram of an exemplary method for delivering noise to a nerve and acquiring information from the nerve.

FIG. 11 shows an exemplary method 1100 to acquire information using one device and to analyze the acquired information using a different device. For example, an implantable device (e.g., the device 100 of FIGS. 1 and 2) may acquire information while an external device 960 or 970 may analyze information acquired by the implantable device. In an alternative arrangement, a patient is fitted with two implantable devices where a first device acquires information and a second device 980 analyzes information acquired by the first device.

Per the method 1100, in an acquisition block 1102, an implantable device acquires information such as nerve activity information from the right and/or left CSN. A storage block 1104 stores the acquired information, for example, as raw data or processed data with optional time markers, etc. During a clinical visit, telephonic communication, etc., another device 960, 970 or 980 pulls the stored information per a communication block 1106. The device 960, 970 or 980 may then, in an analysis block 1108, analyze the information pulled from the other, implantable device. A program block 1110 may be used to program the other, implantable device based at least in part on the analysis of the information. For example, a programmer for an implantable device may include telemetry circuitry, a processor and control logic for performing steps 1106, 1108 and 1110. Such a process may occur according to a schedule, according to occurrence of an event (e.g., arrhythmia, apnea, etc.), or according to a clinician's command. The analysis may help diagnose patient condition and be beneficial in selecting a therapy and/or adjusting a therapy to treat such a condition. In general, carotid sinus nerve information may be acquired at various times, optionally stored and analyzed to determine if a condition is worsening, improving or staying the same.

An exemplary method includes acquiring an electroneurogram of the right carotid sinus nerve or the left carotid sinus nerve, storing the electroneurogram in memory of an implantable device, communicating the stored electroneurogram to another device and analyzing the electroneurogram for at least one of chemosensory information and barosensory information. Such a method may further include calling for one or more therapeutic actions based at least in part on the analyzing and/or instructing the implantable device to call for one or more therapeutic actions based at least in part on the analyzing. Such a method may compare at least one of the chemosensory information and the barosenory information to historic information, for example, to make a diagnosis or to aid in selecting a therapy and/or adjusting a therapy. With respect to making a diagnosis, the diagnosis may include sleep apnea, an increase in metabolic demand, hypoglycemia and hypertension.

An exemplary system includes an implantable device with a processor, memory, a telemetry circuit, a lead bearing one or more electrodes positionable to sense electrical activity of the right carotid sinus nerve or the left carotid sinus nerve and control logic, operable in conjunction with the processor, to store in the memory sensed electrical activity or information derived from the sensed electrical activity and another device (e.g., implantable or external) with a processor, memory, a telemetry circuit and control logic to download, via the telemetry circuit, sensed electrical activity or information derived from the sensed electrical activity from the memory of the implantable device. The download device may include control logic to make a diagnosis based at least in part on the downloaded sensed electrical activity or information derived from the sensed electrical activity and/or include control logic to program one or more operational parameters of the implantable device.

As described herein, the CSN includes many neurons carrying various types of information. To extract or identify particular information, filtering or other techniques (e.g., neural networks, DSP filters, analog filters, wavelets, matched filters, clustering, etc.) may be used, for example, to uncover activity associated with pH, blood pressure, glucose concentration, etc. Techniques to extract or identify particular information may include use of certain electrode designs or configurations.

An exemplary method may identify regions of neurons as carrying particular information. For example, an exemplary method may determine that a region of neurons associated with blood pressure are grouped towards one side of the CSN while neurons carrying information associated with oxygen concentration are grouped to another side, etc. An electrode or electrode array that records activity from a certain portion or portions of the nerve may be used to extract particular information. Where an electrode array allows for multiple electrode configurations, one configuration may be selected to sense one type of nerve activity and another configuration selected to sense another type of nerve activity. Where appropriate, sensing may occur at more than one site along the right CSN and/or the left CSN.

In general, the neuronal diameter population varies within a nerve, and a neuron's diameter often dictates propagation speed of an action potential such that the speed of the action potential increases as the diameter of the neuron increases. Faster action potential propagation speeds have a higher characteristic frequency than a slower propagation speed. An exemplary analysis technique analyzes a CSN electroneurogram to separate out different diameter neurons based on frequency or frequencies (e.g., characteristic frequencies). Also, neurons within a nerve are typically grouped into fascicles based on the origin of the neurons. As fascicles are spatially distributed within a nerve, an exemplary technique may determine fascicle location by recording nerve activity with more than one electrode. By determining the signal's characteristic frequency and fascicle, an exemplary technique may associate a particular type of receptor with a particular type of nerve activity.

An exemplary method may include delivering stochastic noise (e.g., random noise) to a carotid sinus nerve or other nerve as a therapeutic technique to alter a nerve signal. Such a method may deliver the noise sub-threshold to a particular population of nerve fibers of the carotid sinus nerve or other nerve. Certain noise may suffice for a particular population while a different noise may suffice for another population.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method comprising: acquiring an electroneurogram of the right carotid sinus nerve; acquiring an electroneurogram of the left carotid sinus nerve; analyzing the electroneurogram for at least one of chemosensory information and barosensory information wherein the analyzing comprises comparing the electroneurogram of the right carotid sinus nerve to the electroneurogram of the left carotid sinus nerve; and wherein the analyzing comprises subtracting the electroneurogram of the right carotid sinus nerve from the electroneurogram of the left carotid sinus nerve or vice versa; and calling for one or more therapeutic actions based at least in part on the analyzing.

2. The method of claim 1 wherein the analyzing comprises use of at least one established relationship between carotid sinus nerve activity and blood pressure.

3. The method of claim 1 wherein the analyzing comprises use of at least one established relationship between carotid sinus nerve activity and blood chemistry.

4. One or more non-transitory computer-readable storage media comprising processor executable instructions for performing the method of claim 1.

5. The method of claim 1 wherein the analyzing comprises indicating a physiological condition based on the comparing.

6. The method of claim 5 wherein the physiological condition comprises an imbalance in blood flow.

7. A method comprising: acquiring an electroneurogram of the right carotid sinus nerve; acquiring an electroneurogram of the left carotid sinus nerve;
   analyzing the electroneurogram for at least one of chemosensory information and barosensory information wherein the analyzing comprises comparing the electroneurogram of the right carotid sinus nerve to the electroneurogram of the left carotid sinus nerve; and wherein the analyzing comprises determining a time differential based on the comparing; and calling for one or more therapeutic actions based at least in part on the analyzing" right after.

8. The method of claim 7 wherein the determining determines the time differential based on time of a chemosensory response of the right carotid sinus nerve and time of a chemosensory response of the left carotid sinus nerve.

9. The method of claim 7 wherein the determining determines the time differential based on time of a barosensory response of the right carotid sinus nerve and time of a barosensory response of the left carotid sinus nerve.

10. The method of claim 7 wherein the analyzing comprises use of at least one established relationship between carotid sinus nerve activity and blood pressure.

11. The method of claim 7 wherein the analyzing comprises use of at least one established relationship between carotid sinus nerve activity and blood chemistry.

12. One or more non-transitory computer-readable storage media comprising processor executable instructions for performing the method of claim 7.

13. The method of claim 7 wherein the analyzing comprises indicating a physiological condition based on the comparing.

14. The method of claim 13 wherein the physiological condition comprises an imbalance in blood flow.

* * * * *

UNITED STATES PATENT AND TRADEMARK OFFICE
CERTIFICATE OF CORRECTION

| | | |
|---|---|---|
| PATENT NO. | : 7,848,816 B1 | |
| APPLICATION NO. | : 11/964865 | |
| DATED | : December 7, 2010 | |
| INVENTOR(S) | : Wenzel and Farazi | |

It is certified that error appears in the above-identified patent and that said Letters Patent is hereby corrected as shown below:

In the Claims

Column 23, line 24, Claim 7, cancel the text beginning with "7. A method comprising:" to and ending "right after" in column 24, line 6, and insert the following claim:

--7. A method comprising: acquiring an electroneurogram of the right carotid sinus nerve; acquiring an electroneurogram of the left carotid sinus nerve; analyzing the electroneurogram for at least one of chemosensory information and barosensory information wherein the analyzing comprises comparing the electroneurogram of the right carotid sinus nerve to the electroneurogram of the left carotid sinus nerve; and wherein the analyzing comprises determining a time differential based on the comparing; and calling for one or more therapeutic actions based at least in part on the analyzing.--

Signed and Sealed this
Twentieth Day of August, 2013

Teresa Stanek Rea
*Acting Director of the United States Patent and Trademark Office*